United States Patent
Kay et al.

(10) Patent No.: US 6,737,406 B1
(45) Date of Patent: May 18, 2004

(54) CRYPTIC PEPTIDES AND METHOD FOR THEIR IDENTIFICATION

(75) Inventors: Anthony Barrington Kay, London (GB); Mark Larche, Worcester Park (GB)

(73) Assignee: Circassia, Ltd., London (GB)

( * ) Notice: Subject to any disclaimer, the term of this patent is extended or adjusted under 35 U.S.C. 154(b) by 0 days.

(21) Appl. No.: 09/142,885

(22) PCT Filed: Mar. 20, 1997

(86) PCT No.: PCT/GB97/00783

§ 371 (c)(1),
(2), (4) Date: Jan. 27, 1999

(87) PCT Pub. No.: WO97/35193

PCT Pub. Date: Sep. 25, 1997

(30) Foreign Application Priority Data

Mar. 21, 1996 (GB) ................................................. 9605904
Apr. 24, 1996 (GB) ................................................. 9608430

(51) Int. Cl.[7] .............................................. A61K 38/00
(52) U.S. Cl. .......................... 514/13; 530/326; 530/327; 514/14
(58) Field of Search ................. 530/326, 327; 514/13, 14

(56) References Cited

U.S. PATENT DOCUMENTS

| | | | |
|---|---|---|---|
| 5,019,384 A | 5/1991 | Gefter et al. | 424/88 |
| 5,328,991 A | 7/1994 | Kuo | 530/403 |
| 5,547,669 A | 8/1996 | Rogers et al. | 424/185.1 |
| 6,019,972 A | 2/2000 | Gefter et al. | 424/185.1 |
| 6,025,162 A * | 2/2000 | Rogers et al. | 435/69.3 |
| 6,180,368 B1 | 1/2001 | Singh et al. | 435/69.3 |

FOREIGN PATENT DOCUMENTS

| | | | |
|---|---|---|---|
| EP | 0 271 577 | 10/1995 | |
| EP | 0 923 940 A1 | 6/1999 | |
| WO | WO90/11293 | 3/1990 | |
| WO | WO 91/06571 | 5/1991 | |
| WO | WO92/11859 | 1/1992 | |
| WO | WO 92/04445 | 3/1992 | |
| WO | WO 92/07952 | 5/1992 | |
| WO | WO 92/15613 | 9/1992 | |
| WO | WO93/08279 | 10/1992 | |
| WO | WO 93/01213 | 1/1993 | |
| WO | WO94/01560 | 1/1993 | |
| WO | WO94/21675 | 3/1993 | |
| WO | 9308280 | 4/1993 | |
| WO | WO93/21321 | 4/1993 | |
| WO | WO94/24281 | 4/1993 | |
| WO | WO95/06728 | 8/1993 | |
| WO | 9319178 | 9/1993 | |
| WO | WO95/1597 | 12/1993 | |
| WO | WO 94/03478 | 2/1994 | |
| WO | WO 94/05790 | 3/1994 | |
| WO | WO 94/11512 | 5/1994 | |
| WO | WO 94/16068 | 7/1994 | |
| WO | 9427634 | 12/1994 | |
| WO | WO 95/26980 | 10/1995 | |
| WO | WO 95/28424 | 10/1995 | |
| WO | WO96/12737 | 10/1995 | |
| WO | WO96/13589 | 10/1995 | |
| WO | 9607428 | 3/1996 | |
| WO | WO 96/20950 | 7/1996 | |
| WO | 97/33910 | 9/1997 | ......... C07K/14/435 |

OTHER PUBLICATIONS

Mark et al, Human T and B cell immune responses to Fel d 1 in cat–allergic and non–cat allergic subjects, (1996) *Clin Exp Allergy* 26(11): 1316–1328.

van't Hof et al, Epitope mapping of the cat (*Felis domesticus*) major allergen Fel d I by overlapping synthetic peptides and monoclonal anitbodies against native and denatured Fel d I, (1993) *Allergy* 48: 255–263.

Hoyne et al, Regulation of house dust mite responses by intranasally administered peptide: transient activation of $CD4^+$T cells precedes the development of tolerance in vivo, (1996) *Int Immunol* 8(3): 335–342.

Wallner & Gefter, Immunotherapy with T–cell–reactive peptides derived from allergens,(1994) *Allergy* 49: 302–308.

Bacchetta R et al, High levels of interleukin 10 production in vivo are associated with tolerance in SCID patients transplanted with HLA mismatched hematopoietic stem cells,(1994) *J Exp Med* 179(2): 493–502.

Metzler and Wraith, Inhibition of experimental autoimmune encephalomyelitis by inhalation but not oral administration of the encephalitogenic peptide: influence of MHC binding affinity, (1993) *Int. Immunol.* 5: 1159–1165.

Milligen et al., "IgE epitopes on the cat (*Felis domesticus*) major allergen Fel d 1: A study with overlapping synthetic peptides", J. Allergy Clin. Immunol., vol. 93, No. 1, Part 1, pp. 34–43.

Akdis et al (1996) J. Clinic Invest. 98:1676.
Allen et al (1987) Nature 327:713–5.

(List continued on next page.)

*Primary Examiner*—Patrick J. Nolan
(74) *Attorney, Agent, or Firm*—Palmer & Dodge, LLP; Kathleen M. Williams

(57) ABSTRACT

The present invention relates to immunologically cryptic peptides; methods for their identification in individuals and populations and their use in diagnosis and therapy of pathological conditions such as asthma and allergy, and their use in screening for therapeutic activity. Such cryptic peptides are identified by a method which includes the steps of: 1) exposing T cells with the peptide in a primary challenge; 2) measuring the reactivity of T cells with the peptide in the primary challenge of step 1); 3) exposing pre-challenged T cells with the peptide in a secondary challenge, wherein the pre-challenged T cells are obtainable by exposign the T cells to the protein; and measuring the reactivity of the pre-challenged T cells with the peptide in the secondary challenge of step 3), and the peptide is a cryptic peptide if T-cell reactivity is observable in the secondary challenge but not in the primary challenge.

6 Claims, 7 Drawing Sheets

OTHER PUBLICATIONS

Figure 4:
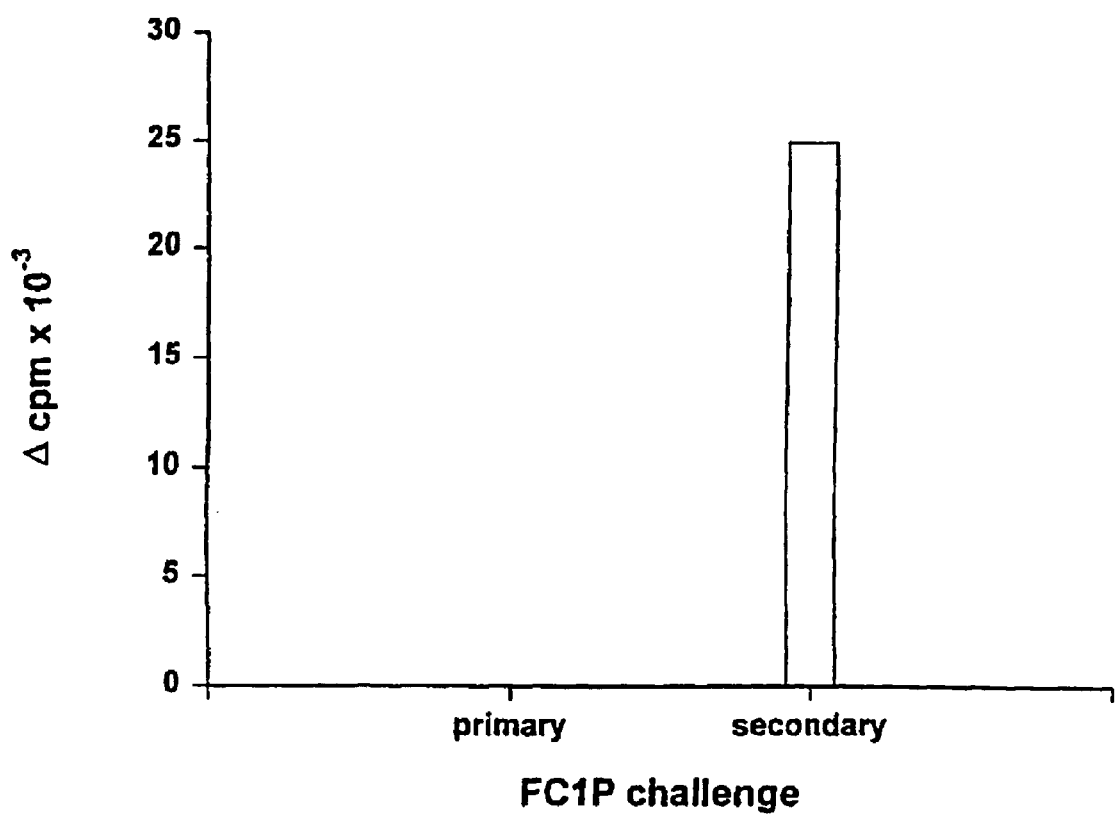

Azzawi et al (1990) Am. Rev. Respir. Dis 142:1407.
Barnes (1999) Nature 402:B31–B38.
Bentley et al (1993) Am. J. Respir. Cell Mol. Biol. 326:298–304.
Bentley et al (1997) Allergy and Allergic Diseases, AB Kay (Ed) Blackwell Science pp. 1113–1130.
Bond et al (1992) J. Allergy Clin. Immunol. 89:320.
Chapman et a; (1988) J. Immunol. 140:812–818.
Chapman and Li (1990) J. Allergy Clin. Immunol 85:170.
Corrigan and Kay (1990) Am. Rev. Respir. Dis. 141:970.
Corrigan and Kay (1992) Immunol. Today 13:501.
Cromwell et al (1986) in *Handbook of Experimental Immunology* (4) Chapter 127, Ed. Weir, DM. Blackwell Scientific Publishers.
Davies et al (1996) J. Immunol. 156:3601–7.
De Groot et al (1988) J. Allergy Clin. Immunol. 82:778–786.
De Sanctis et al (1997) Nature Med. 3:460.
Duffort et al (1991) Molecular Immunol. 28:301–309.
Evavold and Allen (1991) Nature 252:1308–1310.
Garman et al (1992) J. Allergy Clin. Immunol. 89:222.
Haworth et al (1997) "Caucasian England Normal" In: HLA Tissue Typing, Eds. Terasaki and Gjertson. Published by UCLA Tissue Typing Lab.
Herxheimer (1952) Int. Arch. Allergy Appl. Immunol 3:323.
Higgins et al (1994) J. Allerg. Clin. Immunol. 93:891–899.
Hoyne et al (1993) J. Exp. Med. 178:1783.
Hsieh (1985) J. Allergy Clin. Immunology 76:188–194 (Abstract only).
Inoue et al (1997) Int. Arch. Allergy and Immunol. 114:354–360.
Jeffrey et al (1989) Am. Rev. Respir. Dis. 140:1745.
Kon et al (1997) Am. J. Respir.Crit. Care Med. 155:A203 (Abstract).
Laitinen et al (1993) Am. Rev. Repair. Dis. 147:697.
Lanzavecchia (1995) J. Exp. Med 181:1945.
Lehman et al, Nature 358:155.
Leitermann and Ohman (1984) J. Allergy Clin. Immunol. 74(2):147–153.
Li and Chapman (1988) J. Allergy Clin. Immunol. 81(1):308 Abstract No 560.
Litwin et al (1988) Int. Arch Allergy Appl. Immunol. 87:361–366.
MacDonald et al (1995) Science 269–688.
Merzger et al (1987) Am. Rev. Respair. Dis. 135:433.
Meziere et al (1997) J. Immunol. 159:3230–3237.
Mohapatra (1999) in *Immunotherapy in Asthma* Eds. Bousquet J and Yssel H.
Lung Biology in Health and Disease 136:297–312, eds. Marcel Dekker Inc. NY, USA.
Morgenstern et al (1991) J. Allergy Clin. Immunol 87:327.
Norman et al (1996) J. Allergy Clin. Immunol. Abstract 815.
O'Hehir et al (1988) Immunology 64:627–631.
Ohman et al (1984) J. Allergy Clin. Immunol. 74:230–239.
Oldfield et al (2000) J. Allergy and Clin. Immunol. 104:A1111.
Olerup and Zetterquist (1992) Tissue Antigens 29:225–235.
Platt–Mills et al (1998) J. Allergy and Clinical Immunol. 102:335–343.
Qin et al (1993) Science 259:974–7.
Robinson et al (1992) N. England J. Med. 326:298–304.
Santamaria Babi et al (1995) J. Exp. Med. 181:1935–40.
Sihra et al (1997) Thorax 52:447–452.
Sloan–Lancaster et al (1993) Nature 363:156–9.
Smilek et al (1991) PNAS 88:9633–9637.
Van Metre et al (1988) J. Allergy Clin. Immunol. 82:1055–68.
Van Milligen et al (1992) J. Allergy Clin. Immunol. 89:243.
Van Neerven et al (1994) Immunol. 82:351–356.
Watanabe et al (1995) J. Clin. Invest. 96:1303.
Wardlow et al (1995) Adv. Immunol. 60:151.
Wentz et al (1990) J. Allergy Clin. Immunol. 85:94–8.
Wheeler and Drachenberg (1997) Allergy 53:602–612.
Wraith et al (1989) Cell 59:247–255.
Ying et al (1997) J. Immunol. 158:3539–3544.
Yssel et al (1992) J. Immunol. 148:738–745.
Cellular Immunology Labfax, (1994) Tissue and Cell Culture, Chapter 4, p. 5 Delves PJ Ed, Blackwell Scientific Publications.
Scrip (Jul. 8, 1997) No. 2247 p17 "Immunologic's Allervax trail delayed".
Larch, Haselden and Kay (1999) Abstract.
Norman, et al., *American Journal of Respiratory and Critical Care Medicine*, 154:1623–1628 (1996).
Briner, et al., *Proc. Natl. Acad. Sci. USA*, 90:7608–7612 (1993).
Rogers, et al., *Mol. Immunol.*, 31:955–966 (1994).
Counsell, et al., *J. Allergy Clin. Immunol.*, 98(5)Pt.I:884–894 (1996).
Morgenstern, et al., *Proc. Natl. Acad. Sci. USA*, 88:9690–9694 (1991).
Hoyne, et al., *Immunology*, 83:190–195 (1994).
van Neerven, et al., *J. Immunol.*, 152:4203–4207 (1994).
Milligen, et al., *Int. Arch. Allergy Immunol.*, 99:63–73 (1992).
Standring, et al., *Arch. Allergy Appl. Immunol.*, 87:337–341 (1988).
Lamb, et al., *J. Exp. Med.*, 157:1434–1447 (1983).
International Search Report.

* cited by examiner

FIGURE 1

| | |
|---|---|
| Native sequence Chain 1 | EICPAVKRDVDLFLTGTPDEYVEQVAQYKALPVVLENARILKNCVDAKMTEEDKENALSLLDKIYTSPLC |
| Peptide 1 | EICPAVKRDVDLFLT |
| Peptide 2 | RDVDLFLTGTPDEYVE |
| Peptide 3 | GTPDEYVEQVAQYKAL |
| Peptide 4 | EQVAQYKALPVVLENA |
| Peptide 5 | YKALPVVLENARILK |
| Peptide 6 | PVVLENARILKNCVDA |
| Peptide 7 | RILKNCVDAKMTEEDKE |
| Peptide 8 | KMTEEDKENALSLLDK |
| Peptide 9 | NALSLLDKIYTSPLC |

FIGURE 2

Native sequence
Chain 2      VKMAETCPIFYDVFFAVANGNELLLKLSLTKVNATEPERTAMKKIQDCYVENGLISRVLDGLVMTTISSSKDCMGEAVQNTVEDLKLNTLGR Peptide 2.1  VKMAETCPIFYDVFFA Peptide 2.2       IFYDVFFAVANGNE Peptide 2.3            VANGNELLLKLSLTKV Peptide 2.4                   ELLLKLSLTKVNATEPE Peptide 2.5                         NATEPERTAMKKIQD Peptide 2.6                              RTAMKKIQDCYVENGL Peptide 2.7                                     CYVENGLISRVLDGLV Peptide 2.8                                            ISRVLDGLVMTTISSS Peptide 2.9                                                   MTTISSSKDCMGEAV Peptide 2.10                                                         KDCMGEAVQNTVEDLK Peptide 2.11                                                                QNTVEDLKLNTLGR

```
LFLTGTPDEYVEQVAQY
         EQVAQYKALPVVLENA                  FC1P
               KALPVVLENARILKNCV
```

FIGURE 3

CRYPTIC PEPTIDES AND METHOD FOR THEIR IDENTIFICATION

PRIORITY

This application is a National Stage application, under 35 U.S.C. §371, of International Application no. PCT/GB97/00783, filed Mar. 20, 1997, which claims priority to United Kingdom application nos. 9605904.3, filed Mar. 21, 1996, and 9608430.6, filed Apr. 24 1996.

The present invention relates to immunologically cryptic peptides; methods for their identification in individuals and populations and their use in diagnosis and therapy of pathological conditions such as asthma and allergy, and their use in screening for therapeutic activity.

The ability of the immune system to elicit a response to a particular molecule depends critically upon its ability to recognise the presence of an antigen. Classically, the term antigen was associated with the ability of a molecule to be an antibody generator via induction of B-cells. It is now known however that T cells also possess the ability to recognise antigens. T-cell antigen recognition requires antigen presenting cells (APCs) to present antigen fragments (peptides) on their cell surface in association with molecules of the major histocompatibility complex (MHC). T cells use their antigen specific receptors (TCRs) to recognise the antigen fragments presented by the APC. Such recognition acts as a trigger to the immune system to generate a range of responses to eradicate the antigen which has been recognised.

In order to trigger an individual T cell, a critical number of TCRs must be ligated by the peptide/MHC complex presented by the APC. A peptide which reaches the surface of the APC in sufficient numbers to do this can be termed "dominant" or "sub-dominant" depending upon its ability to induce T cell activation relative to other triggering peptides. In the normal course of events i.e. physiologically, a given protein will generate more than one peptide which is capable of triggering a T cell response. The term "dominant" would then be applied to the peptide that induces the most potent or most frequent response. In addition to dominant and sub-dominant epitopes, there are potential T cell peptide epitopes within a given protein sequence (for which T cells are specific), which do not reach the APC surface in sufficient numbers to induce a response. In other words due to the mechanisms of antigen processing within the APC, certain peptides are processed and presented to T-lymphocytes efficiently and therefore stimulate T-cell responses white others are poorly processed and presented to T-lymphocytes. As these latter peptides are not present upon the APC surface in sufficient numbers to stimulate a potentially reactive T-lymphocyte, these peptides have been referred to as "cryptic peptide epitopes".

Cryptic peptide epitopes are present both in proteins normally present in the body (self proteins) and in non-self (or foreign) proteins. In normal physiology, T cells which have the capability of reacting with a cryptic epitope cannot be detected in an in vitro primary stimulation assay (that is, T cells freshly isolated from the blood do not exhibit demonstrable proliferation when cultured with the cryptic peptide). In contrast other peptides which are efficiently processed and presented to T-lymphocytes by APC. can stimulate a proliferative response in primary culture. These are the "dominant" and "sub-dominant" epitopes.

The term "atopic allergy" is applied to a group of allergies characterised by high concentrations of immunoglobulin E (IgE). They include allergic asthma, hay fever, perennial allergic rhinitis, some forms of urticaria (hives) and eczema, allergic conjunctivitis and certain food allergies (particularly food anaphylaxis). The mechanisms of generation of the pathology of such atopic conditions involves not only the synthesis of antigen/allergen specific IgE but also the accompanying differentiation and growth of effector cells such as mast cells and eosinophils.

Allergic IgE-mediated diseases are currently treated by desensitization procedures that involve the periodic injection of allergen components or extracts. Desensitization treatments may induce an IgG response that competes with IgE for allergen, or they may induce specific suppressor T cells that block the synthesis of IgE directed against allergen. This form of treatment is not always effective and poses the risk of provoking serious side effects, particularly general anaphiylactic shock. This can be fatal unless recognised immediately and treated with adrenaline. A therapeutic treatment that would decrease or eliminate the unwanted allergic-immune response to a particular allergen, without altering the immune reactivity to other foreign antigens or triggering an allergic response itself would be of great benefit to allergic individuals.

Sometimes the normal mechanisms whereby self and non-self are immunologically distinguished may break down and an immune response may be elicited against self-antigens present in normal body tissues. This "autoimmunity" generates pathological conditions such as autoimmune thyroiditis, rheumatoid arthritis and lupus erythematosus. Therapeutic regimes are generally limited to the use of anti-inflammatory or immunosuppressive drugs which are relatively non-specific and have many undesirable side-effects.

WO 92111859 describes a method of reducing immune response to an allergen in which a non-allergen derived, non-stimulating peptide which binds to specific MHC class 11 molecules of APCs is used to inhibit T-cell response to particular allergens.

WO 91/06571 purports to disclose peptides derived from human T-cell reactive feline protein which can be used in the diagnosis, treatment or prevention of cat allergy.

WO 94/24281 relates to peptides and modified peptides of the major house dust mite allergens. The modified peptides have the intent of reducing the level of undesirable side effects associated with desensitizing therapies.

G. F. Hoyne et. al. in Immunology 83 pp 190–195 (1994) examined house dust mite allergy using peptides made from cDNA encoding the major allergen DerpI. They purport to show that peptides containing major epitopes can induce oral tolerance in mice to the whole allergen and that it is also possible to induce tolerance with other peptides. Cryptic peptides are suggested as playing a role in this process but no methods are disclosed for their identification or therapeutic use.

None of the above disclosures makes any suggestion that cryptic peptides may play a role in the pathology of atopic conditions such as asthma or other allergic diseases. The present inventors have found a method for identifying cryptic peptides and have observed that individuals with asthma or other allergy-based pathologies have T-lymphocyte populations which can be stimulated in primary culture by cryptic epitopes derived from the allergen which causes the relevant pathology. As described above, T-lymphocytes isolated from a healthy individual would not be expected to be stimulated in primary culture by a cryptic epitope. Likewise in autoimmune pathologies, a self peptide, normally cryptic to the immune system becomes recognised and elicits an immune response.

Hence there is provided according to the invention, a method of determining whether a peptide of a protein is a cryptic peptide, which method includes the steps of: i) exposing T cells with the peptide in a primary challenge; ii) measuring the reactivity of T cells with the peptide in the primary challenge of Step i; iii) exposing pre-challenged T cells with the peptide in a secondary challenge, wherein the pre-challenged T cells are obtainable by exposing the T cells to the protein; and measuring the reactivity of the pre-challenged T cells with the peptide in the secondary challenge.

The prechallenge allows expression of not only dominant and sub-dominant epitopes on the APC surface, but also of any cryptic determinants. The subsequent peptide rechallenge of these cells reveals T-cell reactivity to the dominant, sub-dominant and cryptic epitopes. Primary challenge with peptides will elicit responses from only the normally expressed dominant and sub-dominant epitopes. Thus, peptides recognised following whole antigen primary challenge followed by peptide secondary challenge, but not after peptide primary challenge alone are by definition, cryptic epitopes. The peptide is a cryptic peptide if T-cell reactivity is observable in the secondary challenge above but not in the primary challenge.

The present invention may be illustrated as follows. If peripheral blood mononuclear cells (PBMC) which contain T cells are taken directly from an individual and incubated for a short period of time (e.g. 3–7 days) with a set of synthetic, overlapping peptides from a protein, proliferative responses will be seen to the peptides which T cells recognise in the normal course of events i.e. dominant and sub-dominant epitopes. If however, PBMC are first cultured for 1–2 weeks with a high dose of the whole molecule (or a cocktail of all the peptides), potential T-cell epitopes dominant, sub-dominant and cryptic will then be detected by subsequent "secondary" challenge with the peptides. This is because T-cell populations with any specificity for any of the peptides will have been triggered and expanded (increased in numbers) as a result of the high dose "primary" challenge with whole antigen. By challenging PBMC with the peptides in a primary assay and also a secondary assay, cryptic epitopes can be identified within a population. Therefore any peptide which behaves as a dominant epitope in asthmatics or individuals with a related pathology, but as a cryptic epitope in the normal population can be detected using this method of primary and secondary assay.

In preferred embodiments of the present invention the pre-challenged cells are obtained by exposing the T cells to protein or by exposing the T cells to protein in bulk culture.

The T cells may be obtained from a population comprising a number of individuals (e.g. >20) or from a single individual. If they are obtained from a population then any peptide identified as cryptic in all healthy individuals may be considered to be cryptic within the population in general while use of T cells isolated from a single individual will identify only peptides which are cryptic (or not) in that individual and may not be cryptic in the population.

The steps of the method above may be carried out in the sequence as described or in any alternative sequence known to the person skilled in the art to be suitable to obtain an essentially equivalent result.

In a particularly preferred embodiment of the present invention, the protein from which the peptides are derived is chosen from the list comprising Fel dI (the feline skin and salivary gland allergen of the domestic cat *Felis domesticus*—the amino acid sequence of which is disclosed in WO 91/06571), Der p I, Der p II, Der fI or Der fII (the major protein allergens from the house dust mite dermatophagoides—amino acid sequences disclosed in WO 94/24281) and allergens present in any of the following: grass, tree and weed (including ragweed) pollens; fungi and molds; foods e.g. fish, shellfish, crab, lobster, peanuts, nuts, egg and milk; stinging insects e.g. bee, wasp and hornet and the chironomidae (non-biting midges); spiders and mites: mammals such as dog, horse, rat, guinea pig, mice and gerbil; latex; biological detergent additives; drugs e.g. penicillins and other antibiotics and anaesthetic agents.

More particularly the insect protein from which the peptides may be derived is chosen from the list comprising: housefly, fruit fly, sheep blow fly, screw worm fly, grain weevil, silkworm, honeybee, non-biting midge larvae, bee moth larvae, mealworm, cockroach and larvae of *Tenibrio molitor* beetle. All these being insect allergens of particular relevance to allergic problems arising in the workplace.

Particularly preferred peptides for use in the method of the invention include those shown in FIGS. 1, 2 and 3. The method may also use those shown in any one of Sequence I.D. Nos 25 to 56. The invention also encompasses the use of these peptides as cryptic peptides.

A further aspect of the present invention is any peptide identified as being cryptic when screened by the method of the present invention.

Peptides retaining the ability to bind to MHC class 11 molecules may have up to around 40, preferably 31 residues. Thus, it will be appreciated that useful peptides may comprise a sequence as shown in any one of Sequence I.D. Nos 2 to 10 and 12 to 56. Thus, in one preferred example a 14 mer contiguous sequence forms part of a larger peptide, preferably one up to about 31 residues. In this example the 14 mer forms about 45% of the larger peptide (or polypeptide). Preferably the sequence forms about 50% or more, more preferably about 60% or more, even more preferably about 70% or more, or about 80% or more of the larger peptide. In a specially preferred embodiment the sequence forms about 90% or about 95% or more of the larger sequence.

Yet further aspects of the present invention include a peptide of the present invention, preferably a cryptic peptide when screened by the method of the present invention for use as a medicament or as a diagnostic; the use of a peptide of the present invention, preferably a cryptic peptide when screened by the method of the present invention, in the preparation of a medicament for the treatment of atopic conditions such as asthma; the use of a peptide of the present invention, preferably a cryptic peptide when screened by the method of the present invention, in the preparation of a diagnostic for the diagnosis of atopic conditions such as asthma; a method of preparing a medicament or diagnostic comprising mixing a peptide of the present invention, preferably a cryptic peptide when screened by the method of the present invention, with a suitable carrier, diluent or excipient; the formulations prepared from such uses and methods; a method of therapy and/or diagnosis practised on the human body using a peptide of the present invention, preferably a cryptic peptide.

Whilst it may be possible for the peptides of the present invention to be administered as the raw peptide, it is preferable to present them as a pharmaceutical formulation. According to a further aspect, the present invention provides a pharmaceutical formulation comprising a cryptic peptide together with one or more pharmaceutically acceptable carriers therefor and optionally one or more other therapeutic ingredients. The carrier(s) must be 'acceptable' in the sense of being compatible with the other ingredients of the formulation and not deleterious to the recipient thereof.

The formulations include those suitable for oral (particularly inhaled), parenteral (including subcutaneous, transdermal, intradermal, intramuscular and intravenous and rectal) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the present invention as herein defined or a pharmacologically acceptable salt or solvate thereof ("active ingredient") with the carrier which constitutes one or more accessory ingredients.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Formulations for inhalation may be presented in any of the ways known to be effective e.g. metered does inhalers.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Preferred unit dosage formulations are those containing an effective dose, as hereinbelow recited, or an appropriate fraction thereof, of the active ingredient.

The compounds of the invention may typically be administered orally or via injection at a dose of from 0.001 to 1 mg/kg per day.

The present invention also provides diagnostic kits which comprise cryptic peptides of the present invention. Each kit consists of a microculture plate containing lyophilized peptides corresponding to the cryptic peptide(s) identified by the method of the invention. Each peptide may be present in a minimum of three wells (for statistical evaluation). More replicates may be used depending on the number of peptides to be screened. The use of lyophilized peptides allows the kit to be stored at room temperature for several months before use.

According to a preferred embodiment for carrying out the assay, peripheral blood mononuclear cells (PBMC) may be isolated from patient blood by standard methods. Approximately 20 ml of blood is required. PBMC is added to the wells of the microculture plate in a volume of 200 µl of culture medium containing $10^5$ cells. After 6 days of culture in a humidified incubator at 37° C. gased with 5% $CO_2$ in air, an isotopic label such as $^3$H-thymidine or, a non-isotopic label such as bromo-deoxyuridine is added to each well for a prescribed period (approx. 12–24 hours). Cell proliferation to the peptides present may be assayed in any suitable way, e.g. DNA synthetic analysis, liquid scintillation spectroscopy or colourimetrically.

The measurement of cellular reactivity to peptide challenge according to the present invention is preferably carried out by measurement of cellular proliferation as discussed above. However such reactivity may also be measured by determination of other cellular responses e.g. assay for the release of soluble mediators such as cytokines and chemokines which may demonstrate a release profile indicative of allergic responses.

Cryptic peptides of the present invention which are to be used in therapy may be subject to point mutation in order to avoid certain undesirable side effect of peptide immunotherapy and/or to improve their effects.

Peptide immunotherapy involves the administration of peptides which will disable specific T cells. Data from the trial of Allervax Cat [J. Allergy Clin. Immunol. Jan 1996 Abstract 815] shows that in some patients, a late-phase response to the administered peptide occurs. This response is essentially an asthma attack and represents a serious side-effect of this kind of therapy. By use of "altered peptide ligands" the same therapeutic goals can be achieved i.e., functional elimination of reactive T cells, but without the development of a late-phase response. Having identified a cryptic peptide for therapeutic use, a series of a point mutations may be made to residues in order to generate a panel of closely related peptides. These may be screened for there ability to a) bind to the appropriate MHC molecule with a similar affinity to the original peptide and b) anergise or kill T cells specific for the original peptide. Such altered or synthetic peptides are also encompassed within the present invention.

Particularly preferred synthetic peptides, according to the present invention and for use according to the present invention, include those shown in FIG. 3. Such peptides may be used according to the present invention either individually or in any pairwise or multiple combination thereof.

The pre-challenged T cells may be generated as described above or in one alternative they may be generated by exposure of the T cells to bulk culture or to multiple peptides derived from the protein of interest.

In a particularly preferred embodiment according to the present invention, the method for determining whether a peptide of a protein is a cryptic peptide may be carried out as follows. T cells are isolated from peripheral blood using established techniques [Cellular Immunology LabFax., P. J. Delves (Ed), 1994, Tissue and Cell Culture, Chapter 4, pp. 45. Blackwell Scientific Publications]. A proportion of the cells are cultured in vitro for 6–12 days with the protein of interest. The rest of the cells are aliquoted into cultures and incubated with the peptide of interest derived from the protein. After 3–6 days a label is added to the culture which enables the quantity of DNA synthesis within the cultures to be quantified sometime later (e.g. 8–16 hours later). By analysing the quantity of DNA in the cultures compared to a control culture containing no peptide, it is possible to identify peptide sequences from the protein which stimulate T cells in this "primary" challenge. The group of cells cultured for 6–12 days with whole protein are collected at the end of this culture and washed several times in culture medium. However, as these cells were cultured with whole protein first i.e. were "pre-challenged" the subsequent peptide challenges are referred to as "secondary" challenges. Subsequent analysis of quantities of DNA synthesis in secondary challenges will identify all peptides derived from the protein which can potentially be recognised by T cells within an individual.

In summary, the primary cultures identify the peptides which are recognised by T-lymphocytes from individuals with disease or without disease and the secondary cultures identify all peptides to which T cells can react in individuals with disease or without disease. Epitopes which are cryptic at the population level will be recognised in primary culture by individuals with disease but not by individuals without disease.

T cells according to the present invention may be taken to be any preparation of mononuclear cells obtained from one or more individuals containing T-lymphocytes at a purity sufficient to be able to detect reactivity in a peptide challenge. All technical processes described above may alternatively be carried out using another process known to the person skilled in the art to be able to achieve the desired purpose of that process.

In a further embodiment of the present invention, there is provided the use of cryptic peptides in a compound screen for the identification of compounds possessing therapeutic activity particularly in respect of atopic conditions and more particulary in respect of asthma. In this further embodiment of the present invention the cryptic peptides are preferably those identified using the method of the present invention.

According to this further embodiment of the present invention there is provided both a screening process for the identification of therapeutic compounds and a kit adapted to put such screening process into effect. The screening process of the present invention is preferably carried out in vitro, but may also be carried out in vivo. In a preferred embodiment, the screening process of the present invention may be carried out in vitro as follows. Isolated peripheral blood mononuclear cells or cultured T lymphocytes are cultured in vitro with concentrations of one or more cryptic peptides, preferably previously determined as being optimal for the induction of proliferative and/or other responses in these cells. To certain of the culture wells are added, compounds which are to be screened for their potential to diminish the proliferative response of these cells to the cryptic peptide. Such compounds are preferably added to cultures over a broad range of concentrations. For example, the compound may be added to the cultures at 10-fold dilutions over the range $10^{-12}$M to $10^{-2}$M in order to identify the dose providing the largest diminution in the proliferative response of the cells. Cellular proliferation may be measured using any technique well known in the art, for example cells may be labelled with a compound such as tritiated thymidine which will enable quantification of DNA synthesis and thus cellular proliferation. Compounds capable of diminishing the cellular proliferation induced by the cryptic peptide may be identified as a therapeutic in respect of a medical condition associated with that cryptic peptide. When carried out in vivo, the screening process comprises the administration preferably to a human mammal, of a cryptic peptide to induce a condition associated with that cryptic peptide and the administration, preferably subsequently, of a compound to be screened. A compound capable of diminishing symptoms associated with the induced condition may be identified as a therapeutic in respect of that condition.

Preferably the screen whether in vitro or in vivo comprises the use of cryptic peptides associated with atopic conditions such as asthma and most preferably the use of one or more of the FC1P peptides identified herein.

Non-limiting examples of the invention will now be described with reference to the accompanying Figures, in which:

FIG. 1: shows the native sequence of chain 1 of the major cat allergen Fel d I in single letter amino acid code; and nine peptides derived therefrom. The identifiers for the sequences depicted are as follows: Native sequence Chain 1 (SEQ ID NO:1); Peptide 1 (SEQ ID NO:2); Peptide 2 (SEQ ID NO:3); Peptide 3 (SEQ ID NO: 4); Peptide 4 (SEQ ID NO:5); Peptide 5 (SEQ ID NO:6); Peptide 6 (SEQ ID NO:7); Peptide 7 (SEQ ID NO:8); Peptide 8 (SEQ ID NO:9); Peptide 9 (SEQ ID NO:10)

FIG. 2: shows the native sequence of chain 2 of the major cat allergen Fel d I in single letter amino acid code: and eleven peptides derived therefrom. The identifiers for the sequences depicted are as follows: Native sequence Chain 2 (SEQ ID NO: 11); Peptide 2.1 (SEQ ID NO: 12); Peptide 2.2 (SEQ ID NO: 13); Peptide 2.2 (SEQ ID NO: 14); Peptide 2.3 (SEQ ID NO:15); Peptide 2.4 (SEQ ID NO:16); Peptide 2.5 (SEQ ID NO:17); Peptide 2.6 (SEQ ID NO:18); Peptide 2.7 (SEQ ID NO:18); Peptide 2.8 (SEQ ID NO:19); Peptide 2.9 (SEQ ID NO:20; Peptide 2.10 (SEQ ID NO:21); Peptide 2.11 (SEQ ID NO:22).

FIG. 3: shows three synthetic peptides derived from the sequence of Fel d I. The three peptides are collectively referred to as FC1P. The identifiers for the sequences depicted are as follows: the top sequence (SEQ ID NO:23); the middle sequence (SEQ ID NO:5); the bottom sequence (SEQ ID NO:24).

FIG. 4: shows the results of Example 2 in terms of levels of cellular proliferation (expressed as Δ cpm) in response to primary and secondary challenge of PBMCs with FC1P, as described of PBMCs in the Example.

Figure 5:
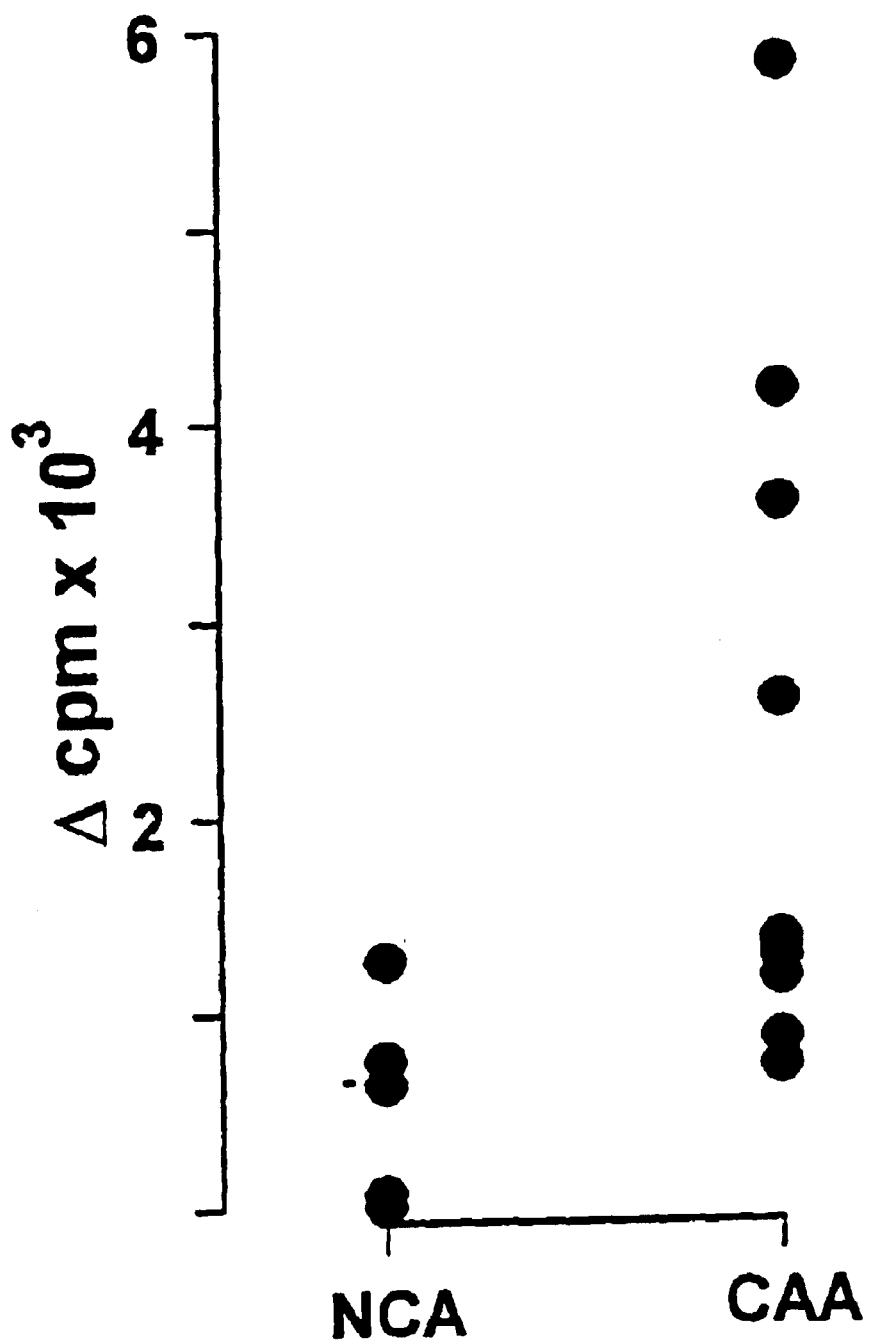

FIG. 5: shows the results of Example 3 in terms of levels of cellular proliferation (expressed as Δ cpm) in response to primary challenge of PBMCs with FC1P, as described in the Example.

Figure 6:
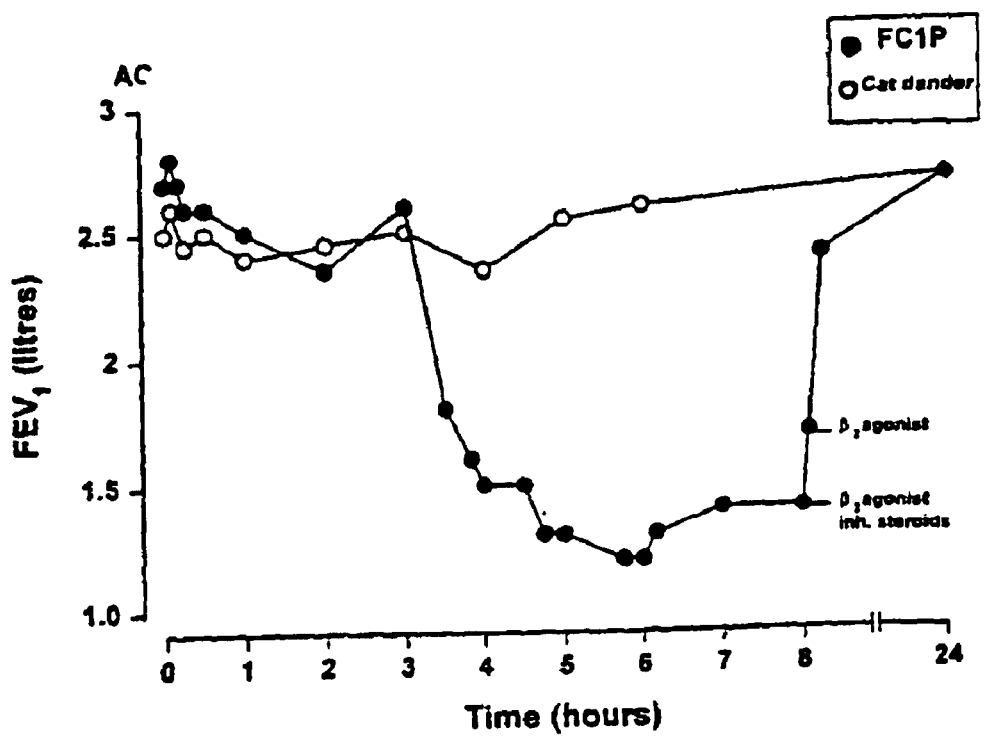

FIG. 6: shows the results of Example 4 in terms of the lung function of an asthmatic (expressed as $FEV_1$ in litres) over time, as a consequence of the factors described in the Example.

Figure 7:
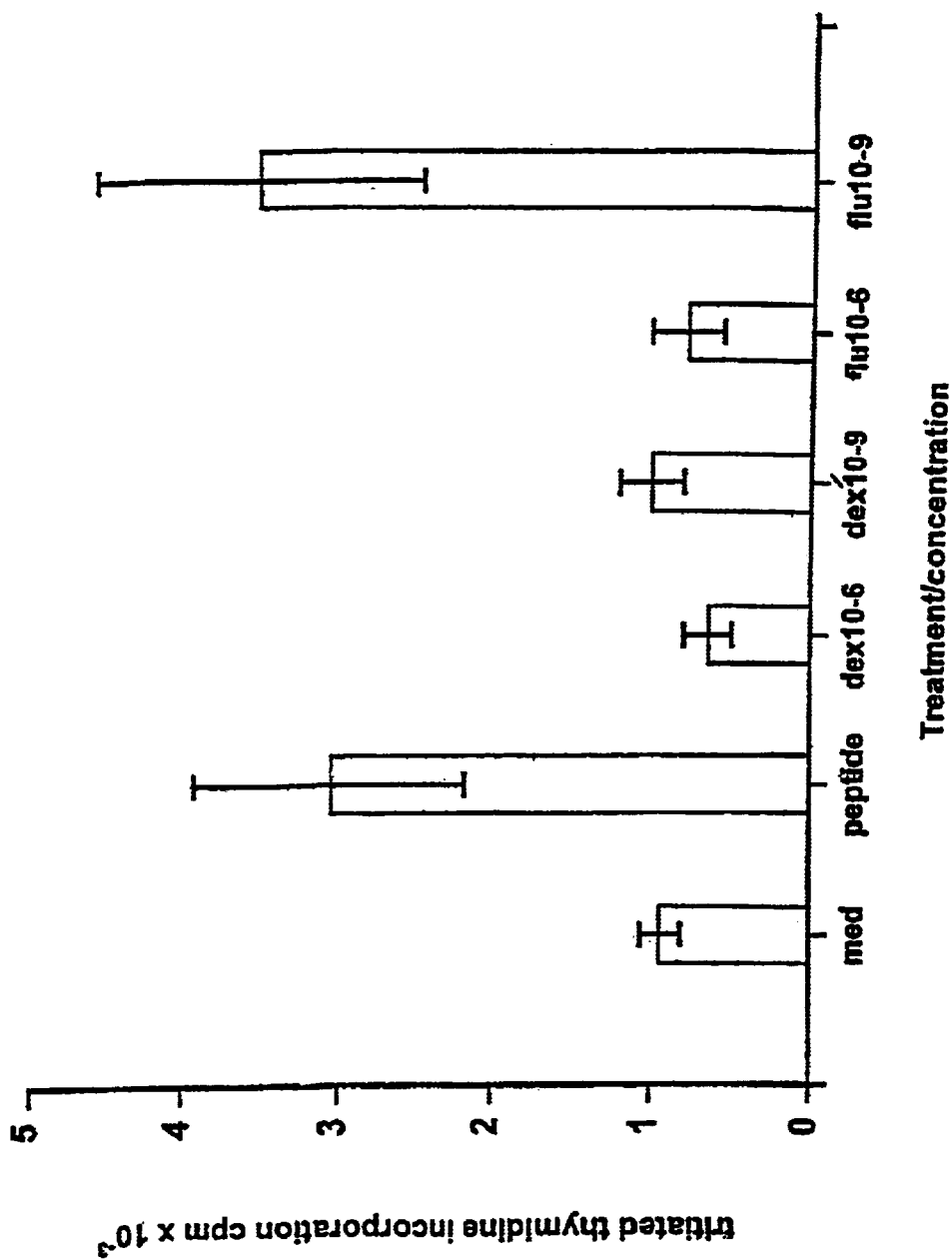

FIG. 7: shows the results of Example 5 in terms of inhibition of T cell proliferation (measured by tritiated thymidine incorporation) to FC1 P peptides by dexamethazone and fluticazone.

EXAMPLE 1

The method for determining whether a peptide of a protein is a cryptic peptide may be carried out as follows.

1—T cells are isolated from peripheral blood,

2—a proportion of the cells are cultured in vitro for 6–12 days with the protein of interest.

3—the rest of the cells are aliquoted into cultures and incubated with the peptide of interest derived from the protein, 4—after 3–6 days a label is added to the culture, enabling the quantity of DNA synthesis within the cultures to be quantified.

5—analysis of the quantity of DNA synthesis in the cultures compared to a control culture containing no peptide, this identifies the peptide sequences from the protein which stimulate T cells in this "primary" challenge, 6—the group of cells cultured for 6–12 days with whole protein are collected at the end of this culture and washed several times in culture medium, 7—analysis of quantities of DNA synthesis in secondary challenges will identify all peptides derived from the protein which can be recognised by T cells within an individual.

The cryptic peptides identified by this method are those stimulating T-cell reactivity in the secondary challenge but not in the primary challenge.

EXAMPLE 2

Peripheral blood mononuclear cells were isolated by density gradient centrifugation. A proportion of the cells were challenged with peptides in primary culture and the remaining cells cultured for 10 days with 100 µg/ml cat dander extract (containing Fel d I). Subsequently, cells cultured with cat dander were collected, washed in culture medium and then cultured for a further three days with the three peptides (at a concentration of 36 µg/ml) which together constitute FC1P (as shown in the FIG. 3 herein) and equal numbers of irradiated autologous feeder cells. Cellular proliferation (expressed as Δ cpm) was quantified by measurement of incorporation of tritiated thymidine into newly synthesised DNA, and is illustrated in FIG. 4.

EXAMPLE 3

Freshly isolated peripheral blood mononuclear cells were cultured at $10^5$ cells per well for 6 days prior to labelling with tritiated thymidine for measurement of cellular proliferation. Cat allergic asthmatics (CAA) demonstrate greater primary proliferative responses to FC1P (36 µm/ml) than do non-cat allergic asthmatics (NCA). The results are shown in FIG. 5.

EXAMPLE 4

40 µg of highly purified FC1P peptides was injected intradermally into each forearm of a volunteer cat-allergic asthmatic. This induced an isolated late-phase asrimatic reaction approximately three hours after administration of FC1P. Lung function (quantified as $FEV_1$) fell and remained low over the next several hours. The drop in $FEV_1$ was reversed by the administration of $\beta_2$ agonist and inhaled corticosteroid at 8 hours. The results of this are shown diagrammatically in FIG. 6.

EXAMPLE 5

Freshly isolated T lymphocytes were cultured in vitro with concentrations of FC1P peptides, previously determined as being optimal for the induction of proliferative and/or other responses in these cells. To certain of the culture wells were added, the glucocorticosteroid Dexamethazone or fluticazone, these were added to cultures at dilutions of $10^{-6}$M or $10^{-9}$M. After culture, cells were labelled with tritiated thymidine to enable quantification of DNA synthesis and thus cellular proliferation. The results are shown in FIG. 7.

---

What is claimed is:

1. A peptide consisting of an amino acid sequence selected from the group consisting of SEQ ID Nos. 2–4, 6–9, 12–21, 25–27, 29–41, 43–46, 48–52, and 54–56.

2. A peptide consisting of SEQ ID NO. 5.

3. A peptide consisting of SEQ ID NO. 23.

4. A peptide consisting of SEQ ID NO. 24.

5. A composition comprising:

at least two peptides, each peptide consisting of an amino acid sequence selected from the group consisting of SEQ ID NO. 5, SEQ ID NO. 23, and SEQ ID NO. 24, wherein each peptide comprises a different amino acid sequence.

6. A composition comprising:

a peptide comprising an amino acid sequence according to SEQ ID NO. 5;

a peptide comprising an amino acid sequence according to SEQ ID NO. 23;

a peptide comprising an amino acid sequence according to SEQ ID NO. 24; and a suitable carrier, diluent, or excipient; wherein the amino acid sequences of said SEQ ID Nos 5, 23, and 24 are different.

* * * * *

SEQUENCE LISTING

<160> NUMBER OF SEQ ID NOS: 56

<210> SEQ ID NO 1
<211> LENGTH: 70
<212> TYPE: PRT
<213> ORGANISM: Felis domesticus

<400> SEQUENCE: 1

```
Glu Ile Cys Pro Ala Val Lys Arg Asp Val Asp Leu Phe Leu Thr Gly
  1               5                  10                  15

Thr Pro Asp Glu Tyr Val Glu Gln Val Ala Gln Tyr Lys Ala Leu Pro
             20                  25                  30

Val Val Leu Glu Asn Ala Arg Ile Leu Lys Asn Cys Val Asp Ala Lys
         35                  40                  45

Met Thr Glu Glu Asp Lys Glu Asn Ala Leu Ser Leu Leu Asp Lys Ile
     50                  55                  60

Tyr Thr Ser Pro Leu Cys
 65                  70
```

<210> SEQ ID NO 2
<211> LENGTH: 15
<212> TYPE: PRT
<213> ORGANISM: Felis domesticus

<400> SEQUENCE: 2

```
Glu Ile Cys Pro Ala Val Lys Arg Asp Val Asp Leu Phe Leu Thr
  1               5                  10                  15
```

<210> SEQ ID NO 3
<211> LENGTH: 16
<212> TYPE: PRT
<213> ORGANISM: Felis domesticus

```
<400> SEQUENCE: 3

Arg Asp Val Asp Leu Phe Leu Thr Gly Thr Pro Asp Glu Tyr Val Glu
 1               5                  10                  15

<210> SEQ ID NO 4
<211> LENGTH: 16
<212> TYPE: PRT
<213> ORGANISM: Felis domesticus

<400> SEQUENCE: 4

Gly Thr Pro Asp Glu Tyr Val Glu Gln Val Ala Gln Tyr Lys Ala Leu
 1               5                  10                  15

<210> SEQ ID NO 5
<211> LENGTH: 16
<212> TYPE: PRT
<213> ORGANISM: Felis domesticus

<400> SEQUENCE: 5

Glu Gln Val Ala Gln Tyr Lys Ala Leu Pro Val Val Leu Glu Asn Ala
 1               5                  10                  15

<210> SEQ ID NO 6
<211> LENGTH: 15
<212> TYPE: PRT
<213> ORGANISM: Felis domesticus

<400> SEQUENCE: 6

Tyr Lys Ala Leu Pro Val Val Leu Glu Asn Ala Arg Ile Leu Lys
 1               5                  10                  15

<210> SEQ ID NO 7
<211> LENGTH: 16
<212> TYPE: PRT
<213> ORGANISM: Felis domesticus

<400> SEQUENCE: 7

Pro Val Val Leu Glu Asn Ala Arg Ile Leu Lys Asn Cys Val Asp Ala
 1               5                  10                  15

<210> SEQ ID NO 8
<211> LENGTH: 17
<212> TYPE: PRT
<213> ORGANISM: Felis domesticus

<400> SEQUENCE: 8

Arg Ile Leu Lys Asn Cys Val Asp Ala Lys Met Thr Glu Glu Asp Lys
 1               5                  10                  15

Glu

<210> SEQ ID NO 9
<211> LENGTH: 16
<212> TYPE: PRT
<213> ORGANISM: Felis domesticus

<400> SEQUENCE: 9

Lys Met Thr Glu Glu Asp Lys Glu Asn Ala Leu Ser Leu Leu Asp Lys
 1               5                  10                  15

<210> SEQ ID NO 10
<211> LENGTH: 15
<212> TYPE: PRT
<213> ORGANISM: Felis domesticus
```

<400> SEQUENCE: 10

Asn Ala Leu Ser Leu Leu Asp Lys Ile Tyr Thr Ser Pro Leu Cys
 1               5                  10                  15

<210> SEQ ID NO 11
<211> LENGTH: 92
<212> TYPE: PRT
<213> ORGANISM: Felis domesticus

<400> SEQUENCE: 11

Val Lys Met Ala Glu Thr Cys Pro Ile Phe Tyr Asp Val Phe Phe Ala
 1               5                  10                  15

Val Ala Asn Gly Asn Glu Leu Leu Lys Leu Ser Leu Thr Lys Val
             20                  25                  30

Asn Ala Thr Glu Pro Glu Arg Thr Ala Met Lys Lys Ile Gln Asp Cys
         35                  40                  45

Tyr Val Glu Asn Gly Leu Ile Ser Arg Val Leu Asp Gly Leu Val Met
     50                  55                  60

Thr Thr Ile Ser Ser Lys Asp Cys Met Gly Glu Ala Val Gln Asn
 65                  70                  75                  80

Thr Val Glu Asp Leu Lys Leu Asn Thr Leu Gly Arg
                 85                  90

<210> SEQ ID NO 12
<211> LENGTH: 16
<212> TYPE: PRT
<213> ORGANISM: Felis domesticus

<400> SEQUENCE: 12

Val Lys Met Ala Glu Thr Cys Pro Ile Phe Tyr Asp Val Phe Phe Ala
 1               5                  10                  15

<210> SEQ ID NO 13
<211> LENGTH: 14
<212> TYPE: PRT
<213> ORGANISM: Felis domesticus

<400> SEQUENCE: 13

Ile Phe Tyr Asp Val Phe Phe Ala Val Ala Asn Gly Asn Glu
 1               5                  10

<210> SEQ ID NO 14
<211> LENGTH: 16
<212> TYPE: PRT
<213> ORGANISM: Felis domesticus

<400> SEQUENCE: 14

Val Ala Asn Gly Asn Glu Leu Leu Leu Lys Leu Ser Leu Thr Lys
 1               5                  10                  15

Val

<210> SEQ ID NO 15
<211> LENGTH: 17
<212> TYPE: PRT
<213> ORGANISM: Felis domesticus

<400> SEQUENCE: 15

Glu Leu Leu Leu Lys Leu Ser Leu Thr Lys Val Asn Ala Thr Glu Pro
 1               5                  10                  15

Glu

```
<210> SEQ ID NO 16
<211> LENGTH: 15
<212> TYPE: PRT
<213> ORGANISM: Felis domesticus

<400> SEQUENCE: 16

Asn Ala Thr Glu Pro Glu Arg Thr Ala Met Lys Lys Ile Gln Asp
 1               5                  10                  15

<210> SEQ ID NO 17
<211> LENGTH: 16
<212> TYPE: PRT
<213> ORGANISM: Felis domesticus

<400> SEQUENCE: 17

Arg Thr Ala Met Lys Lys Ile Gln Asp Cys Tyr Val Glu Asn Gly Leu
 1               5                  10                  15

<210> SEQ ID NO 18
<211> LENGTH: 16
<212> TYPE: PRT
<213> ORGANISM: Felis domesticus

<400> SEQUENCE: 18

Cys Tyr Val Glu Asn Gly Leu Ile Ser Arg Val Leu Asp Gly Leu Val
 1               5                  10                  15

<210> SEQ ID NO 19
<211> LENGTH: 16
<212> TYPE: PRT
<213> ORGANISM: Felis domesticus

<400> SEQUENCE: 19

Ile Ser Arg Val Asp Gly Leu Val Met Ile Thr Thr Ile Ser Ser Ser
 1               5                  10                  15

<210> SEQ ID NO 20
<211> LENGTH: 15
<212> TYPE: PRT
<213> ORGANISM: Felis domesticus

<400> SEQUENCE: 20

Met Thr Thr Ile Ser Ser Ser Lys Asp Cys Met Gly Glu Ala Val
 1               5                  10                  15

<210> SEQ ID NO 21
<211> LENGTH: 16
<212> TYPE: PRT
<213> ORGANISM: Felis domesticus

<400> SEQUENCE: 21

Lys Asp Cys Met Gly Glu Ala Val Gln Asn Thr Val Glu Asp Leu Lys
 1               5                  10                  15

<210> SEQ ID NO 22
<211> LENGTH: 14
<212> TYPE: PRT
<213> ORGANISM: Felis domesticus

<400> SEQUENCE: 22

Gln Asn Thr Val Glu Asp Leu Lys Leu Asn Thr Leu Gly Arg
 1               5                  10
```

```
<210> SEQ ID NO 23
<211> LENGTH: 17
<212> TYPE: PRT
<213> ORGANISM: Felis domesticus

<400> SEQUENCE: 23

Leu Phe Leu Thr Gly Thr Pro Asp Glu Tyr Val Glu Gln Val Ala Gln
 1               5                  10                  15

Tyr

<210> SEQ ID NO 24
<211> LENGTH: 17
<212> TYPE: PRT
<213> ORGANISM: Felis domesticus

<400> SEQUENCE: 24

Lys Ala Leu Pro Val Val Leu Glu Asn Ala Arg Ile Leu Lys Asn Cys
 1               5                  10                  15

Val

<210> SEQ ID NO 25
<211> LENGTH: 14
<212> TYPE: PRT
<213> ORGANISM: Felis domesticus

<400> SEQUENCE: 25

Glu Ile Cys Pro Ala Val Lys Arg Asp Val Asp Leu Phe Leu
 1               5                  10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 26

Ile Cys Pro Ala Val Lys Arg Asp Val Asp Leu Phe Leu Thr
 1               5                  10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 27

Cys Pro Ala Val Lys Arg Asp Val Asp Leu Phe Leu Thr Gly
 1               5                  10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 28

Pro Ala Val Lys Arg Asp Val Asp Leu Phe Leu Thr Gly Thr
 1               5                  10
```

```
<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 29

Ala Val Lys Arg Asp Val Asp Leu Phe Leu Thr Gly Thr Pro
 1               5                  10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 30

Val Lys Arg Asp Val Asp Leu Phe Leu Thr Gly Thr Pro Asp
 1               5                  10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 31

Lys Arg Asp Val Asp Leu Phe Leu Thr Gly Thr Pro Asp Glu
 1               5                  10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 32

Arg Asp Val Asp Leu Phe Leu Thr Gly Thr Pro Asp Glu Tyr
 1               5                  10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 33

Asp Val Asp Leu Phe Leu Thr Gly Thr Pro Asp Glu Tyr Val
 1               5                  10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 34
```

Val Asp Leu Phe Leu Thr Gly Thr Pro Asp Glu Tyr Val Glu
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 35

Asp Leu Phe Leu Thr Gly Thr Pro Asp Glu Tyr Val Glu Gln
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 36

Leu Phe Leu Thr Gly Thr Pro Asp Glu Tyr Val Glu Gln Val
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 37

Phe Leu Thr Gly Thr Pro Asp Glu Tyr Val Glu Gln Val Ala
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 38

Leu Thr Gly Thr Pro Asp Glu Tyr Val Glu Gln Val Ala Gln
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 39

Thr Gly Thr Pro Asp Glu Tyr Val Glu Gln Val Ala Gln Tyr
1               5                   10

<210> SEQ ID NO 40
<211> LENGTH: 14
<212> TYPE: PRT
<213> ORGANISM: Artificial Sequence

```
<220> FEATURE:
<223> OTHER INFORMATION: Description of Artificial Sequence:Cryptic
      peptide derived from allergens

<400> SEQUENCE: 40

Gly Thr Pro Asp Glu Tyr Val Glu Gln Val Ala Gln Tyr Lys
  1               5                  10

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 41

Thr Pro Asp Glu Tyr Val Glu Gln Val Ala Gln Tyr Lys Ala
  1               5                  10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 42

Pro Asp Glu Tyr Val Glu Gln Val Ala Gln Tyr Lys Ala Leu
  1               5                  10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 43

Asp Glu Tyr Val Glu Gln Val Ala Gln Tyr Lys Ala Leu Pro
  1               5                  10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 44

Glu Tyr Val Glu Gln Val Ala Gln Tyr Lys Ala Leu Pro Val
  1               5                  10

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 45

Tyr Val Glu Gln Val Ala Gln Tyr Lys Ala Leu Pro Val Val
  1               5                  10
```

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 46

Val Glu Gln Val Ala Gln Tyr Lys Ala Leu Pro Val Val Leu
 1               5                  10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 47

Glu Gln Val Ala Gln Tyr Lys Ala Leu Pro Val Val Leu Glu
 1               5                  10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 48

Gln Val Ala Gln Tyr Lys Ala Leu Pro Val Val Leu Glu Asn
 1               5                  10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 49

Val Ala Gln Tyr Lys Ala Leu Pro Val Val Leu Glu Asn Ala
 1               5                  10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 50

Ala Gln Tyr Lys Ala Leu Pro Val Val Leu Glu Asn Ala Arg
 1               5                  10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

```
<400> SEQUENCE: 51

Gln Tyr Lys Ala Leu Pro Val Val Leu Glu Asn Ala Arg Ile
 1               5                  10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 52

Tyr Lys Ala Leu Pro Val Val Leu Glu Asn Ala Arg Ile Leu
 1               5                  10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 53

Lys Ala Leu Pro Val Val Leu Glu Asn Ala Arg Ile Leu Lys
 1               5                  10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 54

Ala Leu Pro Val Val Leu Glu Asn Ala Arg Ile Leu Lys Asn
 1               5                  10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 55

Leu Pro Val Val Leu Glu Asn Ala Arg Ile Leu Lys Asn Cys
 1               5                  10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence:Cryptic
      peptide derived from allergens

<400> SEQUENCE: 56

Pro Val Val Leu Glu Asn Ala Arg Ile Leu Lys Asn Cys Val
 1               5                  10
```